United States Patent
Kim (10) Patent No.: US 10,539,569 B2
(45) Date of Patent: Jan. 21, 2020

(54) APPARATUS AND METHOD FOR PROCESSING DATA OF TIME-OF-FLIGHT MASS SPECTROMETRY

(71) Applicant: ASTA Corporation, Suwon-si (KR)

(72) Inventor: Yangsun Kim, Seongnam-si (KR)

(73) Assignee: ASTA Corporation, Suwon-si (KR)

( * ) Notice: Subject to any disclaimer, the term of this patent is extended or adjusted under 35 U.S.C. 154(b) by 73 days.

(21) Appl. No.: 15/875,402

(22) Filed: Jan. 19, 2018

(65) Prior Publication Data
US 2018/0203019 A1 Jul. 19, 2018

Related U.S. Application Data

(60) Provisional application No. 62/447,982, filed on Jan. 19, 2017.

(30) Foreign Application Priority Data

Nov. 24, 2017 (KR) .......................... 10-2017-0158394

(51) Int. Cl.
| | |
|---|---|
| *G01N 33/00* | (2006.01) |
| *G01N 33/68* | (2006.01) |
| *H01J 49/40* | (2006.01) |
| *C12Q 1/04* | (2006.01) |
| *H01J 49/00* | (2006.01) |
| *C12N 1/20* | (2006.01) |

(52) U.S. Cl.
CPC .......... *G01N 33/6848* (2013.01); *C12Q 1/04* (2013.01); *H01J 49/0036* (2013.01); *H01J 49/40* (2013.01); *C12N 1/20* (2013.01); *G01N 2560/00* (2013.01)

(58) Field of Classification Search
CPC ............ G01N 33/6848; G01N 2560/00; H01J 49/0036; H01J 49/40; C12Q 1/04; C12N 1/20
USPC .............. 250/281, 282; 436/173; 435/29, 34
See application file for complete search history.

(56) References Cited

U.S. PATENT DOCUMENTS

2014/0051113 A1* 2/2014 Stephenson, Jr. ........................... G01N 33/6848
435/34

FOREIGN PATENT DOCUMENTS

JP 2015-521035 A 7/2015

OTHER PUBLICATIONS

Krishnamurthy, et al ("Rapid Identification of Bacteria by Direct Matrix-assisted Laser Desorption/Ionization Mass Spectrometric Analysis of Whole Cells" Rapid Comm. Mass Spectrom. 10:1992-1996 (1996) (Year: 1996).*

* cited by examiner

*Primary Examiner* — Michael Maskell
(74) *Attorney, Agent, or Firm* — NSIP Law

(57) ABSTRACT

An apparatus for processing time-of-flight mass spectrometry (TOF MS) data is disclosed. The apparatus may determine at least one candidate microorganism group based on a first molecular weight range in TOF MS data of a sample, determine a second molecular weight range based on a characteristic of the candidate microorganism group in response to a plurality of candidate microorganisms being included in the candidate microorganism group, and identify a microorganism included in the sample from among the candidate microorganisms based on the second molecular weight range in the TOF MS data.

18 Claims, 9 Drawing Sheets

| m/z | Bacillus cereus | | | | | | | | | | | | | |
|---|---|---|---|---|---|---|---|---|---|---|---|---|---|---|
| | KCTC1661 | | | KCTC3624 | | | KCTC3124 | | | KCTC1013 | | | KCTC1508 | |
| 3356.42 | 100.0 | 93.4 | 100.0 | 100.0 | 100.0 | 100.0 | 100.0 | 100.0 | 90.8 | 100.0 | 100.0 | 100.0 | | 3.6 |
| 6712.18 | 77.1 | 100.0 | 72.0 | 51.5 | 49.9 | 54.7 | 76.6 | 81.4 | 77.4 | 57.8 | 42.8 | 57.1 | | |
| 3373.71 | | 12.6 | | 8.8 | 8.9 | 7.1 | | 11.9 | 11.2 | 2.9 | 12.0 | 11.0 | 6.5 | |
| 5194.85 | | | | 3.3 | | | 2.8 | 9.7 | 10.4 | | | 6.2 | | 18.0 |
| 4673.11 | | 3.9 | | 6.0 | | | | | | | | 15.5 | | |
| 3386.81 | | | 3.8 | 6.5 | 4.1 | 3.8 | 6.6 | 7.2 | 7.8 | | | 6.6 | | |
| 3864.88 | | | | | | | 2.1 | | | | | | | |
| 4303.16 | | | | 2.4 | | 2.4 | 2.1 | | | 2.2 | | | 8.8 | 5.1 |
| 3753.53 | | | | | | | | | | | | | 7.2 | 6.1 |

FIG. 3B

| m/z | Bacillus megaterium ||||||||||||||
|---|---|---|---|---|---|---|---|---|---|---|---|---|---|
| | KCTC2194 || KCTC3712 ||| KCTC2178 ||| KCTC13241 ||| KCTC3135 |||
| 3356.42 | 7.5 | 11.8 | 6.5 | 18.3 | 6.5 | 16.2 | 12.2 | 5.4 | 9.6 | 8.3 | 8.3 | 11.4 | 7.1 | |
| 6712.18 | | 8.1 | | 15.8 | | | | | 6.0 | | 7.3 | | | 8.1 |
| 3373.71 | 11.6 | 57.5 | 40.2 | 15.5 | 32.9 | 56.1 | 10.5 | 26.8 | 52.6 | 8.0 | 52.9 | 44.5 | 9.2 | 67.8 |
| 5194.85 | 40.9 | 94.7 | 55.8 | 62.0 | 55.2 | 87.4 | 46.2 | 73.9 | 72.1 | 28.1 | 83.0 | 80.7 | 20.3 | 96.0 |
| 4673.11 | 16.4 | 49.6 | 14.9 | 21.5 | 20.2 | 44.3 | 17.8 | 24.6 | 22.3 | | 35.6 | 31.6 | | 49.1 |
| 3386.81 | 11.1 | 49.1 | 28.0 | 17.4 | 21.5 | 59.0 | 8.7 | 21.9 | 44.7 | 9.8 | 34.4 | 32.0 | | 47.6 |
| 3864.88 | 12.6 | 52.8 | 29.3 | 20.8 | 31.2 | 46.2 | 9.8 | 31.5 | 45.5 | 10.1 | 47.8 | 42.1 | 17.7 | 73.1 |
| 4303.16 | 46.6 | 100.0 | 60.9 | 46.1 | 60.1 | 68.2 | 52.5 | 100.0 | 69.1 | 20.5 | 93.3 | 94.7 | 9.3 | 92.4 |
| 3753.53 | 12.3 | 61.5 | 34.4 | 22.8 | 29.3 | 53.4 | 18.6 | 30.1 | 53.5 | 7.0 | 46.0 | 38.7 | 6.8 | 62.6 |

(First data column under each strain has additional values: KCTC2194: 64.9, 89.6, 38.4, 58.6, 51.5, 97.0, 63.2)

FIG. 3C

| m/z | KCTC1014 | | | KCTC3452 | | | Bacillus thuringiensis | | | | | | | | |
|---|---|---|---|---|---|---|---|---|---|---|---|---|---|---|---|
| | | | | | | | KCTC1511 | | | KCTC1507 | | | KCTC1316 | | |
| 3356.42 | 100.0 | 100.0 | 100.0 | | | 7.9 | 100.0 | 100.0 | 100.0 | 100.0 | 100.0 | 100.0 | 100.0 | 100.0 | 92.2 |
| 6712.18 | 74.7 | 63.4 | 84.1 | | | | 63.9 | 66.3 | 85.1 | 63.8 | 67.9 | 73.9 | 60.1 | 83.4 | 100.0 |
| 3373.71 | 12.6 | 10.0 | 11.9 | 3.9 | | 7.6 | 13.4 | 9.2 | | 8.3 | 10.3 | 8.3 | | 8.9 | 9.0 |
| 5194.85 | 9.0 | | 8.0 | | | | 7.3 | | 8.3 | | | | | | |
| 4673.11 | 7.5 | 6.6 | 9.2 | | | | 6.7 | 4.9 | 9.9 | 2.0 | | 3.1 | | | |
| 3386.81 | 9.3 | | 7.6 | | | | | 4.4 | 6.7 | | 4.8 | | | 3.8 | |
| 3864.88 | | | | 5.6 | 8.7 | | | | | | | | | | |
| 4303.16 | | | | 3.8 | 7.1 | | | | | | | | | | |
| 3753.53 | | | | | | 8.1 | | | 10.8 | | | | | | |

FIG. 4A

| m/z | Bacillus cereus KCTC3624 ||||||||
|---|---|---|---|---|---|---|---|---|
| | 1 day ||| 2day ||| 3 day |||
| 714.20 | 100.0 | 100.0 | 100.0 | 38.6 | 100.0 | 71.8 | 3.4 | 100.0 | 100.0 |
| 892.84 | | | 2.2 | 10.0 | 32.0 | 22.7 | | 0.8 | |
| 906.50 | | | 1.4 | | | 7.7 | | | |

FIG. 4B

| m/z | Bacillus cereus KCTC3124 ||||||||
|---|---|---|---|---|---|---|---|---|
| | 1 day ||| 2day ||| 3 day |||
| 714.20 | 100.0 | 100.0 | 100.0 | 10.5 | 100.0 | 100.0 | 4.1 | 100.0 | 100.0 |
| 892.84 | 2.6 | 1.4 | 7.5 | 4.5 | 8.3 | 6.9 | 0.7 | 7.6 | |
| 906.50 | 1.7 | 1.0 | 2.6 | 1.1 | | 4.5 | 0.3 | | |

FIG. 4C

| m/z | Bacillus cereus KCTC1013 ||||||||
|---|---|---|---|---|---|---|---|---|
| | 1 day ||| 2day ||| 3 day |||
| 714.20 | 100.0 | 100.0 | 99.3 | 14.4 | 100.0 | 66.6 | | | 100.0 |
| 892.84 | 8.6 | | 7.0 | 2.9 | 6.7 | 14.8 | 0.5 | | |
| 906.50 | | | 3.2 | 0.9 | | | | | |

FIG. 4D

| m/z | Bacillus thuringiensis KCTC1014 ||||||||| 
|---|---|---|---|---|---|---|---|---|---|
| | 1 day ||| 2day ||| 3 day |||
| 714.20 | 17.7 | 30.1 | 23.2 | 1.6 | 4.2 | 5.7 | | 91.1 | 31.9 |
| 892.84 | 30.2 | 48.9 | 25.4 | 30.4 | 41.8 | 27.1 | | | |
| 906.50 | 100.0 | 100.0 | 100.0 | | 100.0 | 100.0 | 100.0 | | 100.0 |

FIG. 4E

| m/z | Bacillus thuringiensis KCTC1511 |||||||||
|---|---|---|---|---|---|---|---|---|---|
| | 1 day ||| 2day ||| 3 day |||
| 714.20 | 32.8 | 8.2 | 63.3 | 5.2 | 20.7 | 19.2 | 25.2 | 99.4 | 29.3 |
| 892.84 | 43.1 | 65.5 | 36.8 | 36.0 | 77.2 | 28.9 | | 100.0 | |
| 906.50 | 100.0 | 100.0 | 100.0 | | 100.0 | 100.0 | 98.2 | | |

FIG. 4F

| m/z | Bacillus thuringiensis KCTC1507 |||||||||
|---|---|---|---|---|---|---|---|---|---|
| | 1 day ||| 2day ||| 3 day |||
| 714.20 | 26.0 | 34.9 | 48.9 | 2.6 | 6.9 | 16.4 | | 70.6 | |
| 892.84 | 40.2 | 50.1 | 52.7 | 32.0 | 40.9 | 45.8 | | 86.5 | |
| 906.50 | | 100.0 | 100.0 | | 100.0 | | 100.0 | 100.0 | 100.0 |

FIG. 5

FIG. 6

APPARATUS AND METHOD FOR PROCESSING DATA OF TIME-OF-FLIGHT MASS SPECTROMETRY

CROSS-REFERENCE TO RELATED APPLICATIONS

This application claims the benefit under 35 U.S.C. § 119(e) of U.S. Provisional Application No. 62/447,982 filed on Jan. 19, 2017, in the U.S. Patent and Trademark Office and Korean Patent Application No. 10-2017-0158394 filed on Nov. 24, 2017, in the Korean Intellectual Property Office, the entire disclosures of which are incorporated herein by reference for all purposes.

BACKGROUND

1. Field

The following description relates to a data processing apparatus and method, and more particularly, to an apparatus and method that may process data obtained as a result of performing time-of-flight mass spectrometry (TOF MS) on a sample and may identify a microorganism in the sample based on the processed data.

2. Description of Related Art

Mass spectrometry (MS) is used to isolate ions based on mass of each of the ions and detect the ions, and time-of-flight (TOF) MS refers to a method using a simple principle among various MS-based methods. In detail, the TOF MS is used to analyze mass of an ion based on an amount of time used for the ion, which is accelerated in an electric field and has a speed, to travel a certain distance to a detector at the speed.

The speed, or an acceleration, of the ion may change based on a force received by the electric field and the mass. For example, a light ion may be rapidly accelerated and a heavy ion may be slowly accelerated and they thus arrive at the detector at different times. Herein, using such a TOF MS to convert a TOF distribution to a mass spectrum, information associated with a target sample may be obtained.

However, when performing microbial species identification, or microbial identification, on a sample through the TOF MS, it may not be easy to identify an accurate species only using a general method of analyzing peak intensity in a mass spectrum.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a microbial identification apparatus includes a candidate group determiner configured to determine a candidate microorganism group based on a first molecular weight range in time-of-flight mass spectrometry (TOF MS) data of a sample, and an identification processor configured to determine a second molecular weight range based on a characteristic of the candidate microorganism group in response to a plurality of candidate microorganisms being included in the candidate microorganism group, and identify a microorganism included in the sample from among the candidate microorganisms based on the second molecular weight range in the TOF MS data.

The first molecular weight range may include a range associated with ribosomal protein.

The second molecular weight range may include a range of molecular weights that are smaller compared to molecular weights of the first molecular weight range.

The second molecular weight range may include a molecular weight range of 500 to 3000 daltons (Da).

The second molecular weight range in the TOF MS data may be associated with a range in which an m/z value in the TOF MS data is 500 to 1000.

The candidate microorganism group may include *Bacillus cereus* and *Bacillus thuringiensis*.

In another general aspect, a microbial identification apparatus includes a candidate group receiver configured to receive, from an external interface, a candidate microorganism group including a plurality of candidate microorganisms, and an identification processor configured to determine a reference molecular weight range based on a characteristic of the candidate microorganism group, and identify a microorganism included in a sample from among the candidate microorganisms based on the reference molecular weight rage in TOF MS data of the sample.

The reference molecular weight range may include a molecular weight range of 500 to 3000 Da.

The reference molecular weight range in the TOF MS data may be associated with a range in which an m/z value in the TOF MS data is 500 to 1000.

In still another general aspect, a method of processing TOF MS data of a sample, the method, includes determining a candidate microorganism group based on a first molecular weight range in the TOF MS data, determining a second molecular weight range based on a characteristic of the candidate microorganism group in response to a plurality of candidate microorganisms being included in the candidate microorganism group, and identifying a microorganism included in the sample from among the candidate microorganisms based on the second molecular weight range in the TOF MS data.

The first molecular weight range may include a range associated with ribosomal protein.

The second molecular weight range may include a range of molecular weights that are smaller compared to molecular weights of the first molecular weight range.

The second molecular weight range may include a molecular weight range of 500 to 3000 Da.

The second molecular weight range in the TOF MS data may be associated with a range in which an m/z value in the TOF MS data is 500 to 1000.

The candidate microorganism group may include *Bacillus cereus* and *Bacillus thuringiensis*.

In yet another general aspect, a method of processing TOF MS data of a sample, the method, includes receiving, from an external interface, a candidate microorganism group including a plurality of candidate microorganisms, and determining a reference molecular weight range based on a characteristic of the candidate microorganism group and identifying a microorganism included in the sample from among the candidate microorganisms based on the reference molecular weight range in the TOF MS data.

The reference molecular weight range may include a molecular weight range of 500 to 3000 Da.

The reference molecular weight range in the TOF MS data may be associated with a range in which an m/z value in the TOF MS data is 500 to 1000.

In a further general aspect, an apparatus for processing TOF MS data of a sample, the apparatus, includes a candidate group determiner configured to determine a candidate substance group based on a first molecular weight range in the TOF MS data, and an identification processor configured to determine a second molecular weight range based on a characteristic of the candidate substance group in response to a plurality of candidate substances being included in the candidate substance group, and identify a substance included in the sample from among the candidate substances based on the second molecular weight range in the TOF MS data.

In still another general aspect, a method of processing TOF MS data of a sample, the method, includes determining a candidate substance group based on a first molecular weight range in the TOF MS data, determining a second molecular weight range based on a characteristic of the candidate substance group in response to a plurality of candidate substances being included in the candidate substance group, and identifying a substance included in the sample from among the candidate substances based on the second molecular weight range in the TOF MS data.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Also, in the description of embodiments, detailed description of well-known related structures or functions will be omitted when it is deemed that such description will cause ambiguous interpretation of the present disclosure.

Figure 1:
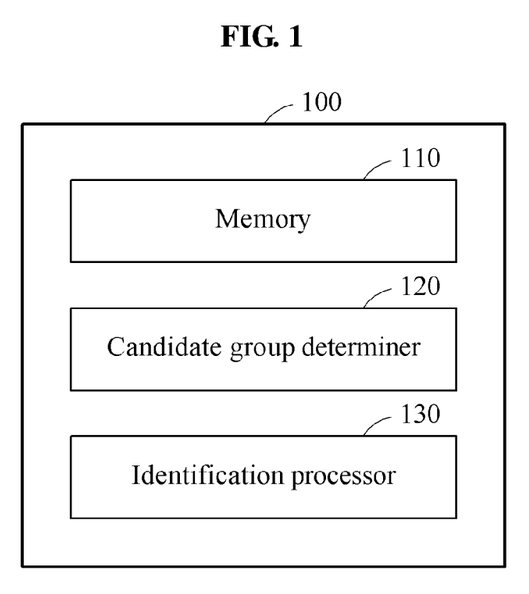
FIG. 1 is a diagram illustrating an example of an apparatus for processing time-of-flight mass spectrometry (TOF MS) data.

FIG. 1 is a diagram illustrating an example of an apparatus for processing time-of-flight mass spectrometry (TOF MS) data. Hereinafter, an apparatus for processing TOF MS data will be simply referred to as a TOF MS data processing apparatus. According to an example embodiment, a TOF MS data processing apparatus 100 may be a microbial identification apparatus. Referring to FIG. 1, the TOF MS data processing apparatus 100 includes a memory 110, a candidate group determiner 120, and an identification processor 130.

The memory 110 stores TOF MS data of a sample. The memory 110 may be a component used to store data on which microbial identification to be described hereinafter is based, and may be embodied in a suitable form, for example, an additionally provided storage device or processor, an internal memory embedded in a chip, and the like. The TOF MS data of the sample may be stored as a peak intensity value based on m/z.

The candidate group determiner 120 performs primary identification to determine a candidate microorganism group based on a first molecular weight range in the TOF MS data. For example, the candidate group determiner 120 may identify at least one candidate microorganism based on data of a ribosomal protein spectrum. A molecular weight range associated with ribosomal protein may correspond to, for example, approximately 10000 to 30000 daltons (Da).

When only a single microbial species is present in the candidate microorganism group determined through the primary identification, the microbial species may be verified as a microorganism included in the sample, without a need to perform an additional process.

However, when a plurality of microbial species is present in the candidate microorganism group determined through the primary identification, it may not be simple to identify a microbial species based on a ribosomal protein spectrum used for a general TOF MS method, and it may not be possible to immediately verify an accurate result of microbial identification due to a potential error and such included in a result of the microbial identification.

The following is a list of candidate microorganism groups that are known to be difficult to accurately identify microbial species therein through matrix-assisted laser desorption ionization (MALDI)-TOF MS.

1. *Acinetobacter baumannii/Acinetobacter nosocomialis/Acinetobacter pittii*
2. *Acinetobacter bereziniae/Acinetobacter guillouiae*
3. *Achromobacter denitrificans/Achromobacter xylosoxidans/Achromobacter insolitus*
4. *Bacillus cereus/Bacillus thuringiensis*
5. *Burkholderia cepacia/Burkholderia cenocepacia*
6. *Candida lipolytica/Candida pelliculosa*
7. *Citrobacter braakii/Citrobacter freundii/Citrobacter youngae*
8. *Corynebacterium propinquum/Corynebacterium pseudodiphtheriticum*
9. *Elizabethkingia meningoseptica/Elizabethkingia miricola*
10. *Enterobacter asburiae/Enterobacter cloacae/Enterobacter kobei*
11. *Escherichia coli/Escherichia fergusonii/Shigella* species (*S. sonnei, S. boydii, S. flexneri, S. dysenteriae*)
12. *Neisseria flavescens/Neisseria macacae/Neisseria mucosa/Neisseria perflava*
13. *Serratia marcescens/Serratia ureilytica*
14. *Streptococcus oralis/Streptococcus mitis/Streptococcus pneumoniae*
15. *Veillonella caviae/Veillonella denticariosi/Veillonella dispar/Veillonella parvula/Veillonella rogosae*
16. *Vibrio alginolyticus/Vibrio parahaemolyticus*
17. *Mycobacterium tuberculosis/Mycobacterium bovis/Mycobacterium caprae*
18. *Mycobacterium intracellulare/Mycobacterium chimaera*
19. *Mycobacterium phocaicum/Mycobacterium mucogenicum*

In a case of *Bacillus cereus* and *Bacillus thuringiensis*, as a representative example of such candidate microorganism groups, a difference between them in terms of a peak intensity profile in a range associated with ribosomal protein in a result of the MALDI-TOF MS is not distinctive, and thus identification may fail or an incorrect identification result may be obtained.

As already known, *Bacillus cereus* is a bacterium that may cause foodborne illnesses and *Bacillus thuringiensis* is an insect-related pathogen, whose characteristics differ from each other. Thus, when there is an error in microbial identification or accuracy is not ensured for the microbial identification, a fatal issue may occur. Thus, according to example embodiments described herein, additional identification may be performed on a candidate microorganism group in which microorganisms have not been easy to be accurately identified by using general-type MALDI-TOF MS.

The identification processor 130 determines a second molecular weight range for secondary identification, or the additional identification, based on a characteristic of the candidate microorganism group, in response to a plurality of candidate microorganisms being included in the candidate microorganism group.

In detail, when determining a second molecular weight range suitable for each candidate microorganism group, information associated with a range in which a plurality of candidate microorganisms included in each candidate microorganism group exhibits different peak intensities may be collected. Herein, it may be desirable to collect such information by constructing a database in advance based on sufficient cases. However, it may also be possible to process such information in real time.

When such a range in which a plurality of candidate microorganisms included in a candidate microorganism group exhibits different peak intensities is discovered, the range may be determined to be a second molecular weight range for secondary identification of the corresponding candidate microorganism group.

For example, in a case of *Bacillus cereus* and *Bacillus thuringiensis*, they exhibit peak intensity profiles that are not clearly distinguishable from each other in a general ribosomal protein spectrum range. However, they exhibit a distinguishable difference in a small molecule range. Thus, a second molecular weight range for *Bacillus cereus* and *Bacillus thuringiensis* may be determined to be, for example, a small molecule range of approximately 500 to 3000 Da. A peak intensity profile of each of *Bacillus cereus* and *Bacillus thuringiensis* will be described in greater detail with reference to the following drawings.

The identification processor 130 performs the secondary identification based on the determined second molecular weight range. For example, the identification processor 130 may finally determine which microorganism among the candidate microorganisms included in the candidate microorganism group is included in the sample, based on the second molecular weight range in the TOF MS data.

Figure 2:
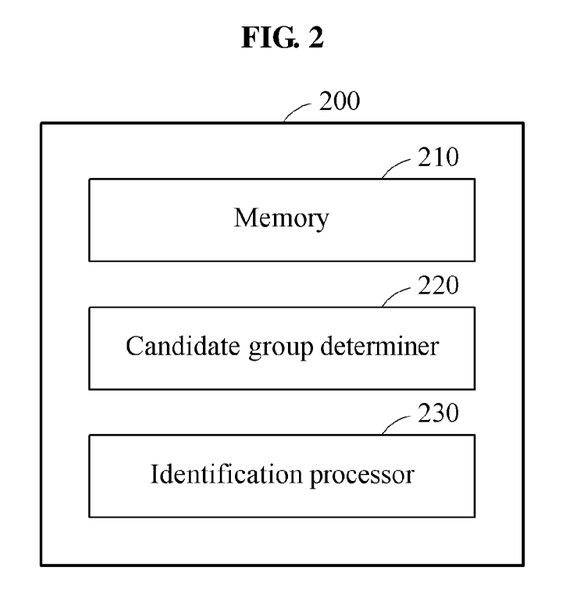
FIG. 2 is a diagram illustrating another example of an apparatus for processing TOF MS data.

FIG. 2 is a diagram illustrating another example of a TOF MS data processing apparatus. According to an example, a TOF MS data processing apparatus 200 may be a microbial identification apparatus. Referring to FIG. 2, the TOF MS data processing apparatus 200 includes a memory 210, a candidate group receiver 220, and an identification processor 230.

The memory 210 stores therein TOF MS data of a sample. The memory 210 may be a component used to store data on which microbial identification to be described hereinafter is based, and may be embodied in a suitable form, for example, an additionally provided storage device or processor, an internal memory embedded in a chip, and the like. The TOF MS data of the sample may be stored as peak intensity values based on m/z.

The candidate group receiver 220 receives, from an external interface, a candidate microorganism group includ- 
ing a plurality of candidate microorganisms. For example, a candidate microorganism group including a plurality of candidate microorganism on which precise microbial identification is to be performed may be received through a wired or wireless communication device.

Although the candidate microorganism group including the candidate microorganisms is verified through primary identification by an external device, only the primary identification may not fully ensure accuracy in determining which microorganism among the candidate microorganisms is included in the sample, and thus additional identification or re-identification may be required. The primary identification may be performed using other microbial identification methods, in addition to MALDI-TOF MS.

In a case in which a microorganism, which is a target for identification, is highly likely to be included in a certain candidate microorganism group, or only whether the microorganism is a candidate microorganism or not in the candidate microorganism group needs to be determined rapidly, the candidate microorganism group may be received without the primary identification. Example embodiments described herein may also be applicable to various cases or situations as necessary.

The identification processor 230 determines a reference molecular weight range for identification based on a characteristic of the received candidate microorganism group.

In detail, when determining a reference molecular weight range suitable for a candidate microorganism group, information associated with a range in which a plurality of candidate microorganisms included in the candidate microorganism group exhibits different peak intensities may be collected. It may be desirable to collect such information by constructing a database in advance based on sufficient cases. However, it may also be possible to process such information in real time.

When such a range in which candidate microorganisms in a candidate microorganism group exhibit different peak intensities is observed, the range may be determined to be a reference molecular weight range for identification within the candidate microorganism group.

The identification processor 230 performs the identification on the candidate microorganism group based on the determined reference molecular weight range. For example, the identification processor 230 may determine which microorganism among the candidate microorganisms included in the candidate microorganism group is included in the sample, based on the reference molecular weight range in the TOF MS data.

Figure 3A:
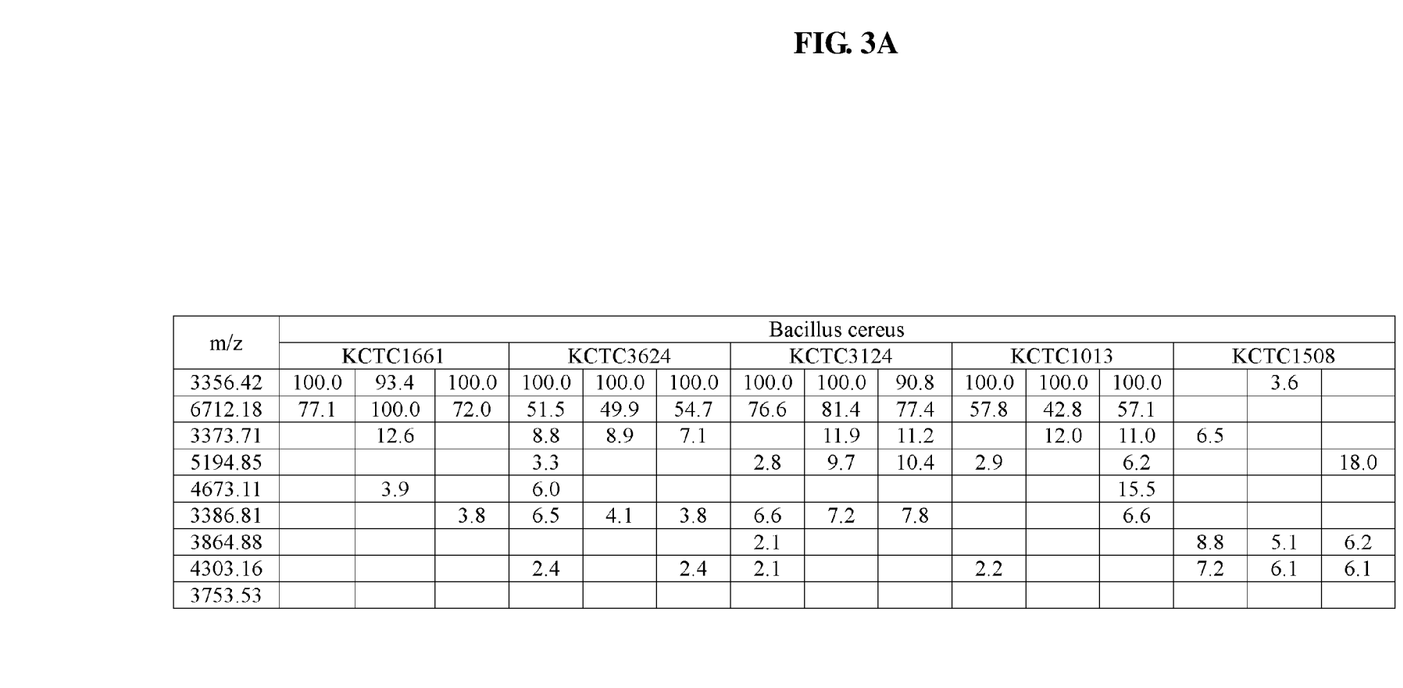
FIGS. 3A through 3C are diagrams illustrating examples of TOF MS data.
Figure 3B:
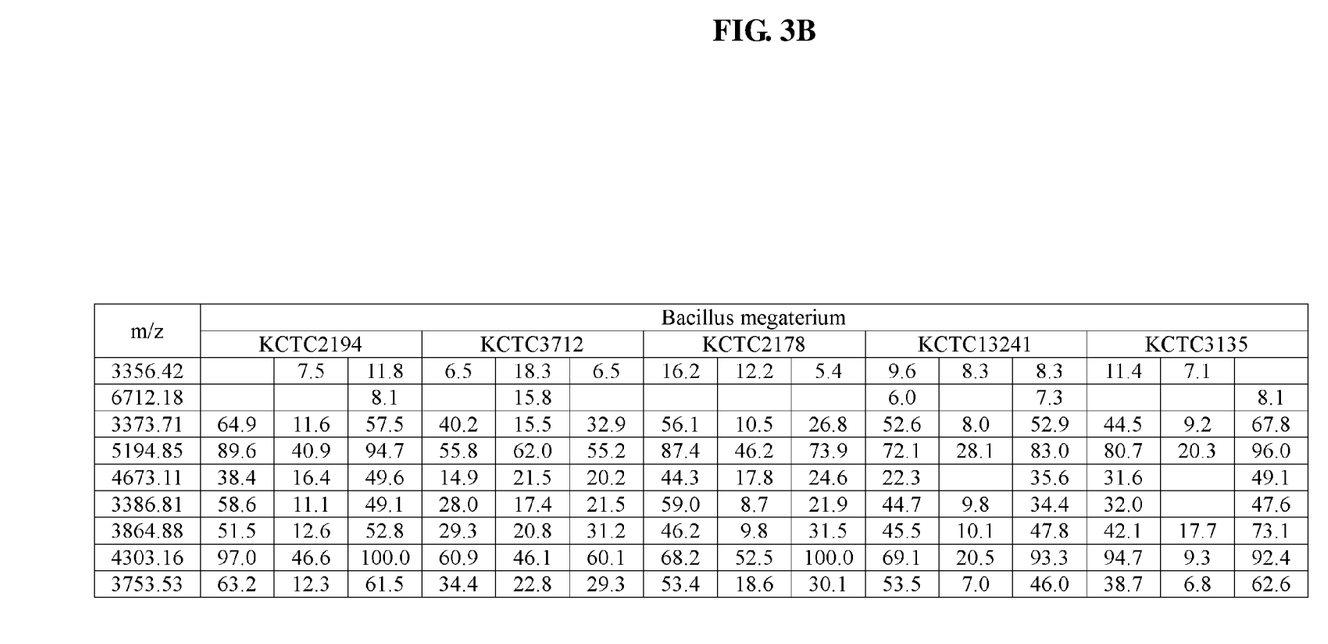
Figure 3C:
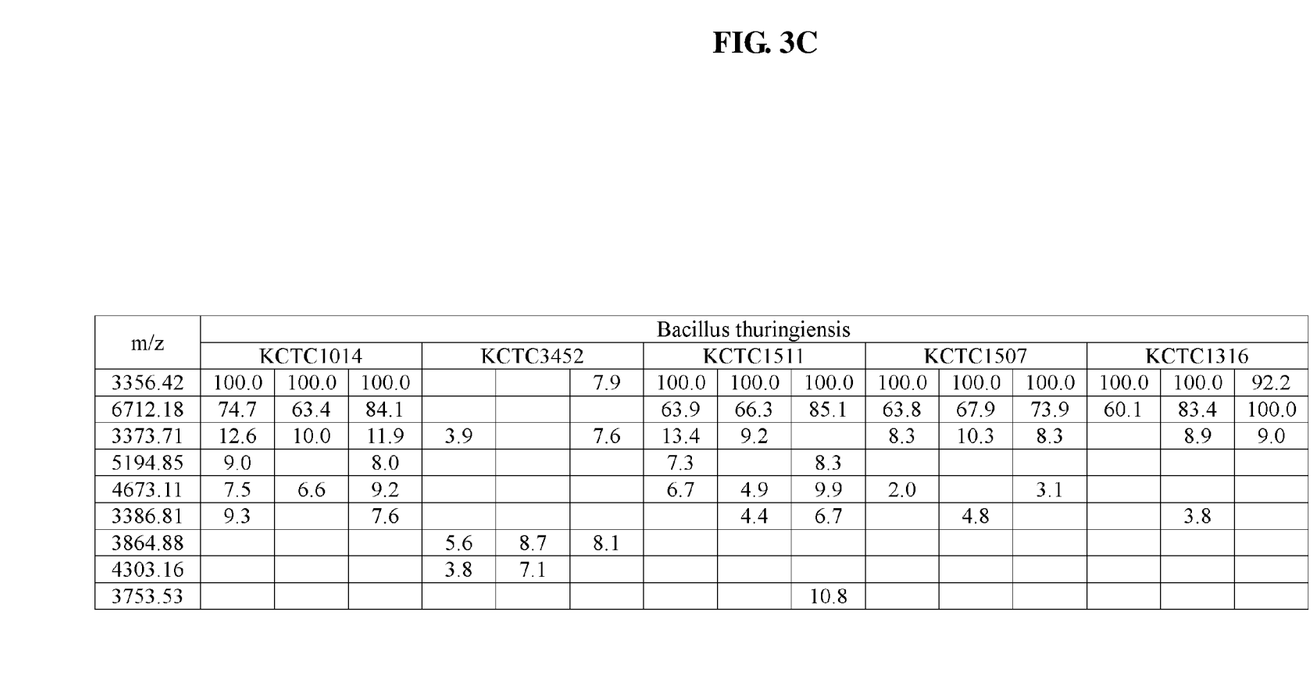
Figure 4A:
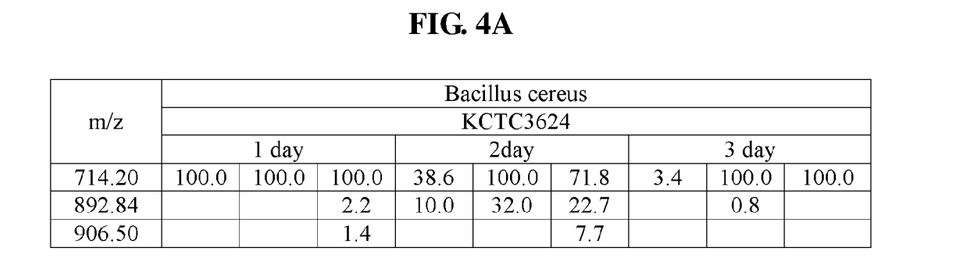
FIGS. 4A through 4F are diagrams illustrating other examples of TOF MS data.
Figure 4B:
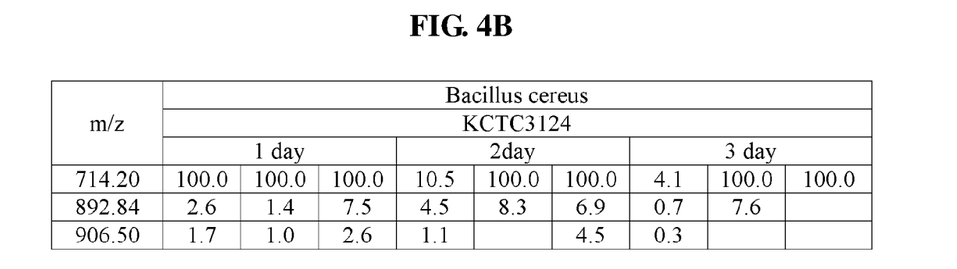
Figure 4C:
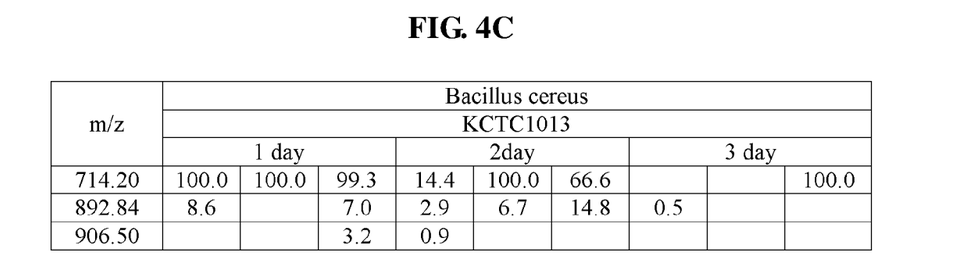
Figure 4D:
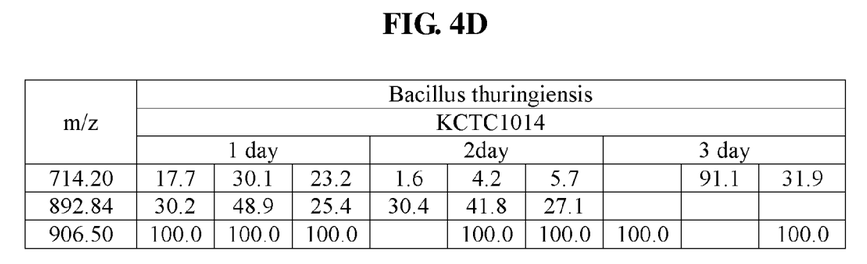
Figure 4E:
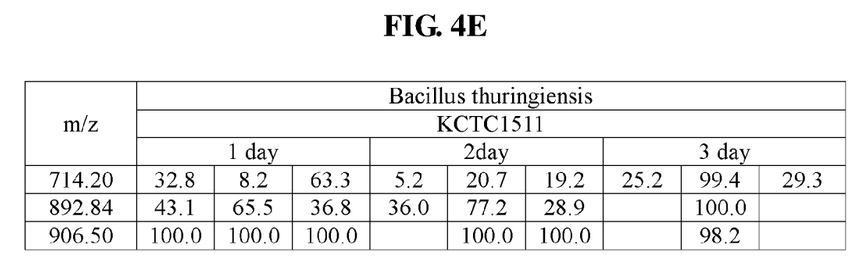
Figure 4F:
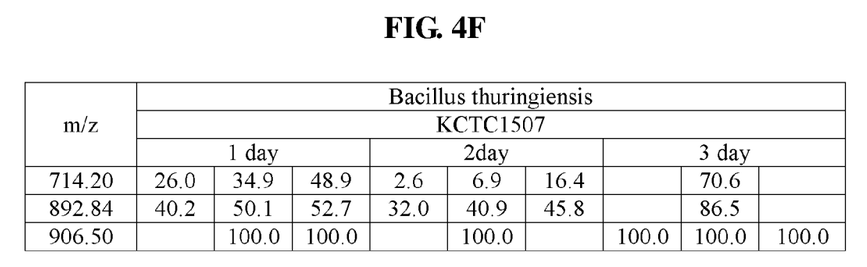

FIGS. 3A through 3C are diagrams illustrating examples of TOF MS data. FIG. 3A is a diagram illustrating an example result of MALDI-TOF MS performed on *Bacillus cereus*, and FIGS. 3B and 3C are diagrams illustrating respective example results of MALDI-TOF MS performed on *Bacillus megaterium* and *Bacillus thuringiensis*.

Referring to FIGS. 3A and 3C, *Bacillus cereus* and *Bacillus thuringiensis* exhibit high peak intensities at m/z values of 3356.42 and 6712.18. Referring to FIG. 3B, *Bacillus megaterium* exhibits high peak intensities at m/z values of 3373.71, 5194.85, 4673.11, 3386.81, 3864.88, 4303.16, and 3753.53.

Thus, it may be relatively easy to identify *Bacillus megaterium* using such peak intensity profiles illustrated in FIGS. 3A through 3C. However, in a case of *Bacillus cereus* and *Bacillus thuringiensis*, they have similar peak intensity profiles, and thus accurate microbial identification may not be readily performed only using mass spectra in illustrated ranges.

However, it is observed through experiments that *Bacillus cereus* and *Bacillus thuringiensis* are distinguishable from each other in a small molecule range, although they have peak intensity profiles that are not clearly distinguishable in a general ribosomal protein spectrum range. Thus, based on such a characteristic, additional identification may be performed on a candidate microorganism group including *Bacillus cereus* and *Bacillus thuringiensis* using data corresponding to the small molecule range.

FIGS. 4A through 4F are diagrams illustrating other examples of TOF MS data. FIGS. 4A through 4C are diagrams illustrating example results of MALDI-TOF MS performed on *Bacillus cereus*, and FIGS. 4D through 4F are diagrams illustrating example results of MALDI-TOF MS performed on *Bacillus thuringiensis*.

Referring to FIGS. 4A through 4C, *Bacillus cereus* exhibits high peak intensities at an m/z value of 714.20. Referring to FIGS. 4D through 4F, *Bacillus thuringiensis* exhibits high peak intensities at m/z values of 892.84 and 906.50.

Thus, it is possible to perform accurate microbial identification on *Bacillus cereus* and *Bacillus thuringiensis* using such peak intensity profiles in a small molecule range as illustrated in FIGS. 4A through 4F. In detail, *Bacillus cereus* and *Bacillus thuringiensis* may be more clearly distinguished from each other by selecting a molecular weight range of 500 to 3000 Da or a range in which an m/z value is 500 to 1000, and processing corresponding data.

The illustrated experiment result data and microorganism types are provided merely as examples, and thus examples suggested herein are not limited to such illustrated microorganism types and numerical values provided above.

FIG. 5 is a flowchart illustrating an example of a method of processing TOF MS data. Hereinafter, a method of processing TOF MS data will be simply referred to as a TOF MS data processing method. The TOF MS data processing method to be described hereinafter with reference to FIG. 5 may be performed by a TOF MS data processing apparatus, for example, the TOF MS data processing apparatus 100 illustrated in FIG. 1.

Referring to FIG. 5, in operation 510, the TOF MS data processing apparatus determines a candidate microorganism group based on a first molecular weight range in TOF MS data of a sample. For example, the TOF MS data processing apparatus may identify at least one candidate microorganism based on data of a ribosomal protein spectrum. In a case in which only a single microbial species is present in the candidate microorganism group, the microbial species may be determined to be a microorganism included in the sample without an additional process. However, in a case in which a plurality of microbial species is present in the candidate microorganism group, additional identification may be performed through the following operations from operation 520.

In operation 520, the TOF MS data processing apparatus determines a second molecular weight range based on a characteristic of the candidate microorganism group. Herein, information associated with a range in which a plurality of candidate microorganisms included in the candidate microorganism group exhibits different peak intensities may be collected in advance. When such a range in which the candidate microorganisms exhibit the different peak intensities is observed, the range may be determined to be the second molecular weight range for secondary identification of the candidate microorganism group.

In operation 530, the TOF MS data processing apparatus identifies a microorganism included in the sample from among the candidate microorganisms based on the second molecular weight range in the TOF MS data. For example, the TOF MS data processing apparatus may finally determine which microorganism among the candidate microorganisms included in the candidate microorganism group is included in the sample, based on the second molecular weight range in the TOF MS data.

By performing microbial identification using TOF MS data corresponding to a second molecular weight range determined based on a characteristic of a candidate microorganism group through such operations described above, accuracy of a result of the microbial identification may be enhanced and a data throughput may also be optimized.

Figure 6:
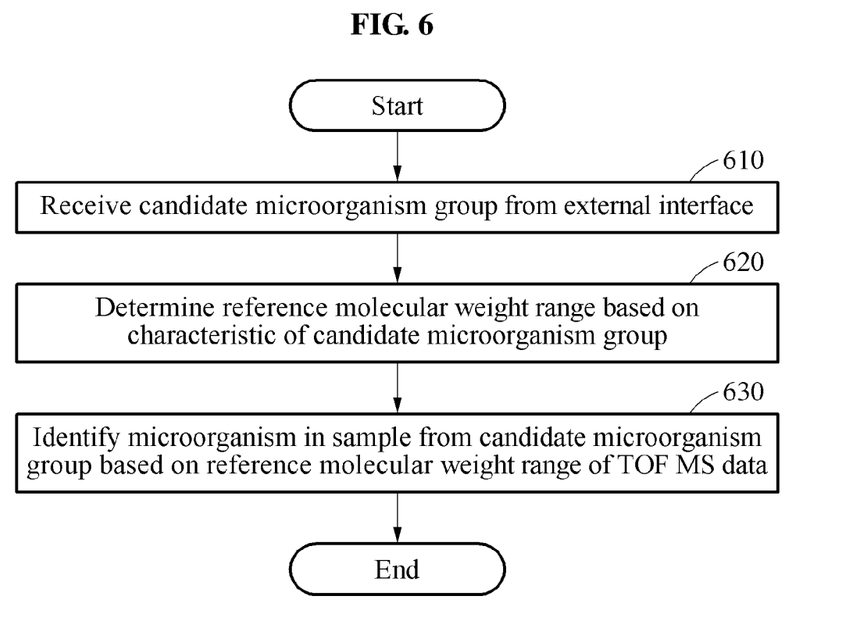
FIG. 6 is a flowchart illustrating another example of a method of processing TOF MS data.

FIG. 6 is a flowchart illustrating another example of a TOF MS data processing method. The TOF MS data processing method to be described hereinafter with reference to FIG. 6 may be performed by a TOF MS data processing apparatus, for example, the TOF MS data processing apparatus 200 illustrated in FIG. 2.

Referring to FIG. 6, in operation 610, the TOF MS data processing apparatus receives a candidate microorganism group from an external interface. The candidate microorganism group to be received may be verified through primary identification by an external device. However, the primary identification may not be sufficient to accurately identify which microorganism among a plurality of candidate microorganisms in the candidate microorganism group is included in a sample, and thus additional identification or re-identification may be required. In a case in which a microorganism, which is a target for identification, is highly likely to be included in a certain candidate microorganism group, or only whether the microorganism is a candidate microorganism or not in the candidate microorganism group needs to be determined rapidly, the candidate microorganism group may be received without the primary identification.

In operation 620, the TOF MS data processing apparatus determines a reference molecular weight range based on a characteristic of the candidate microorganism group. Herein, information associated with a range in which the candidate microorganisms included in the candidate microorganism group exhibit different peak intensities may be collected in advance. When such a range in which the candidate microorganisms exhibit the different peak intensities is observed, the range may be determined to be the reference molecular weight range for identification within the candidate microorganism group.

In operation 630, the TOF MS data processing apparatus identifies a microorganism included in the sample from among the candidate microorganisms included in the candidate microorganism group based on the reference molecular weight range in the TOF MS data. For example, the TOF MS data processing apparatus may finally determine which microorganism among the candidate microorganisms included in the candidate microorganism group is included in the sample, based on the reference molecular weight range in the TOF MS data.

By performing microbial identification using TOF MS data corresponding to a certain molecular weight range determined based on a characteristic of a candidate microorganism group through such operations described above, accuracy of a result of the microbial identification may be enhanced and a data throughput may also be optimized.

The TOF MS data processing apparatus or the microbial identification apparatus described herein, and other apparatuses, units, modules, devices, and other components described herein with respect to FIGS. 1 and 2 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

Figure 5:
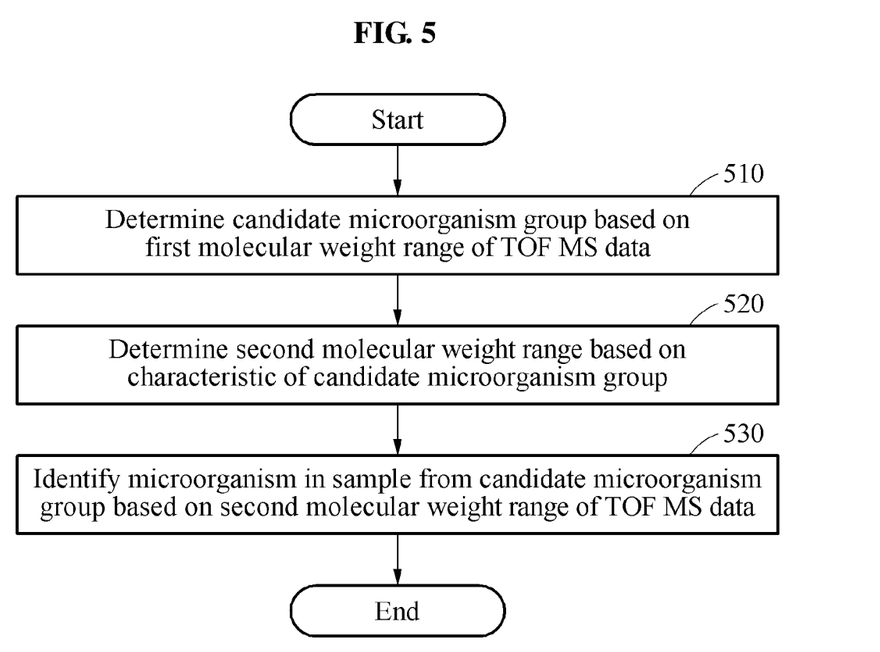
FIG. 5 is a flowchart illustrating an example of a method of processing TOF MS data.

The methods illustrated in FIGS. 5 and 6 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A microbial identification apparatus comprising:
   a candidate group determiner configured to determine a candidate microorganism group based on a first molecular weight range in time-of-flight mass spectrometry (TOF MS) data of a sample; and
   an identification processor configured to determine a second molecular weight range based on a characteristic of the candidate microorganism group in response to a plurality of candidate microorganisms being included in the candidate microorganism group, and identify a microorganism included in the sample from among the candidate microorganisms based on the second molecular weight range in the TOF MS data,
   wherein the second molecular weight range, in which each of the plurality of candidate microorganisms exhibits at least one peak intensity at a molecular weight different from that of another, is a range of molecular weights smaller than molecular weights of the first molecular weight range.

2. The microbial identification apparatus of claim 1, wherein the first molecular weight range includes a range associated with ribosomal protein.

3. The microbial identification apparatus of claim 1, wherein the second molecular weight range includes a molecular weight range of 500 to 3000 daltons (Da).

4. The microbial identification apparatus of claim 1, wherein the second molecular weight range in the TOF MS data is associated with a range in which an m/z value in the TOF MS data is 500 to 1000.

5. The microbial identification apparatus of claim 1, wherein the candidate microorganism group includes *Bacillus cereus* and *Bacillus thuringiensis*.

6. A microbial identification apparatus comprising:
   a candidate group receiver configured to receive, from an external interface, a candidate microorganism group including a plurality of candidate microorganisms; and
   an identification processor configured to determine a reference molecular weight range, in which each of the plurality of candidate microorganisms exhibits at least one peak intensity at a molecular weight different from that of another, based on a characteristic of the candidate microorganism group, and identify a microorganism included in a sample from among the candidate microorganisms based on the reference molecular weight range in time-of-flight mass spectrometry (TOF MS) data of the sample.

7. The microbial identification apparatus of claim 6, wherein the reference molecular weight range includes a molecular weight range of 500 to 3000 daltons (Da).

8. The microbial identification apparatus of claim 6, wherein the reference molecular weight range in the TOF MS data is associated with a range in which an m/z value in the TOF MS data is 500 to 1000.

9. A method of processing time-of-flight mass spectrometry (TOF MS) data of a sample, the method comprising:
   determining a candidate microorganism group based on a first molecular weight range in the TOF MS data;
   determining a second molecular weight range based on a characteristic of the candidate microorganism group in response to a plurality of candidate microorganisms being included in the candidate microorganism group; and
   identifying a microorganism included in the sample from among the candidate microorganisms based on the second molecular weight range in the TOF MS data, wherein the second molecular weight range, in which each of the plurality of candidate microorganisms exhibits at least one peak intensity at a molecular weight different from that of another, is a range of molecular weights smaller than molecular weights of the first molecular weight range.

10. The method of claim 9, wherein the first molecular weight range includes a range associated with ribosomal protein.

11. The method of claim 9, wherein the second molecular weight range includes a molecular weight range of 500 to 3000 daltons (Da).

12. The method of claim 9, wherein the second molecular weight range in the TOF MS data is associated with a range in which an m/z value in the TOF MS data is 500 to 1000.

13. The method of claim 9, wherein the candidate microorganism group includes *Bacillus cereus* and *Bacillus thuringiensis*.

14. A method of processing time-of-flight mass spectrometry (TOF MS) data of a sample, the method comprising:
receiving, from an external interface, a candidate microorganism group including a plurality of candidate microorganisms; and
determining a reference molecular weight range, in which each of the plurality of candidate microorganisms exhibits at least one peak intensity at a molecular weight different from that of another, based on a characteristic of the candidate microorganism group, and identifying a microorganism included in the sample from among the candidate microorganisms based on the reference molecular weight range in the TOF MS data.

15. The method of claim 14, wherein the reference molecular weight range includes a molecular weight range of 500 to 3000 daltons (Da).

16. The method of claim 14, wherein the reference molecular weight range in the TOF MS data is associated with a range in which an m/z value in the TOF MS data is 500 to 1000.

17. An apparatus for processing time-of-flight mass spectrometry (TOF MS) data of a sample, the apparatus comprising:
a candidate group determiner configured to determine a candidate substance group based on a first molecular weight range in the TOF MS data; and
an identification processor configured to determine a second molecular weight range based on a characteristic of the candidate substance group in response to a plurality of candidate substances being included in the candidate substance group, and identify a substance included in the sample from among the candidate substances based on the second molecular weight range in the TOF MS data,
wherein the second molecular weight range, in which each of the plurality of candidate microorganisms exhibits at least one peak intensity at a molecular weight different from that of another, is a range of molecular weights smaller than molecular weights of the first molecular weight range.

18. A method of processing time-of-flight mass spectrometry (TOF MS) data of a sample, the method comprising:
determining a candidate substance group based on a first molecular weight range in the TOF MS data;
determining a second molecular weight range based on a characteristic of the candidate substance group in response to a plurality of candidate substances being included in the candidate substance group; and
identifying a substance included in the sample from among the candidate substances based on the second molecular weight range in the TOF MS data,
wherein the second molecular weight range, in which each of the plurality of candidate microorganisms exhibits at least one peak intensity at a molecular weight different from that of another, is a range of molecular weights smaller than molecular weights of the first molecular weight range.

* * * * *